United States Patent [19]

Doyle

[11] Patent Number: 4,843,242

[45] Date of Patent: Jun. 27, 1989

[54] INFRARED MICROSCOPE EMPLOYING A PROJECTED FIELD STOP

[75] Inventor: Walter M. Doyle, Laguna Beach, Calif.

[73] Assignee: Laser Precision Corporation, Irvine, Calif.

[21] Appl. No.: 921,066

[22] Filed: Oct. 20, 1986

[51] Int. Cl.$^4$ ............................................. G02B 21/00
[52] U.S. Cl. .................................. 250/330; 250/338.1; 250/341; 350/527
[58] Field of Search .................... 250/330, 341, 338 R, 250/353, 332; 350/1.2, 505, 527; 356/346

[56] References Cited

U.S. PATENT DOCUMENTS

| | | | |
|---|---|---|---|
| 3,933,408 | 1/1976 | Reinert | 350/523 |
| 4,113,344 | 9/1978 | Shoemaker | 350/526 |
| 4,594,509 | 6/1986 | Simon et al. | 250/338 |

OTHER PUBLICATIONS

IR Plan, "An Added Dimension in Microscopy and FT-IR", Spectra Tech. brochure.
Leitz-MPV System publication, "Structure of the Leitz-MPV System", undated.
BIO RAD Publication, Cambridge, MA, undated.

Primary Examiner—Carolyn E. Fields
Assistant Examiner—John A. Miller
Attorney, Agent, or Firm—Thomas J. Plante

[57] ABSTRACT

An infrared microscope is disclosed in which two adjustable field stops are included. One is used to determine the illuminated area at the sample when the microscope is used in the transmission mode. The other is used to determine the illuminated area at the sample when the microscope is used in the reflectance mode. The latter field stop is imaged in the plane of the former; and the radiation in the reflectance mode passes through the former field stop both as it passes to the sample and as it returns from the sample after reflectance.

8 Claims, 3 Drawing Sheets

INFRARED MICROSCOPE EMPLOYING A PROJECTED FIELD STOP

BACKGROUND OF THE INVENTION

This invention relates to microscopes which are used in infrared (IR) sample analysis, and particularly to the use of such microscopes in the reflectance mode, i.e., in situations in which the incoming modulated radiation is reflected at the sample. Such reflection may be caused by the sample itself, or by an adjacent reflecting surface which causes radiation to pass through the sample.

As disclosed in an earlier application of the same inventor, having a common assignee, identified as application Ser. No. 907,995, filed Sep. 16, 1986, a relatively high radiation throughput for reflectance in an FTIR microscope can be attained by using a fully reflecting "injection" mirror to direct half of a post-interferometer radiation beam through the objective lens toward the sample. The returning IR beam reflected at the sample passes again through the objective lens, bypasses the injection mirror, and reaches the detector. The collimated beam entering the microscope from the interferometer is focused and then recollimated by two confocal parabolic mirrors before the beam reaches the injection This system provides four image planes, (in which the radiation is brought to a focus) one at the sample, one at the detector, a third between the objective lens and the detector, and a fourth between the two confocal parabolic mirrors.

In any infrared microscope, it is important to be able to limit the area being analyzed, while providing a visible means for positively identifying the extent of this area. In transmission microscopy, this is generally accomplished quite simply by locating a variable size (adjustable) field stop, or iris, in a plane which contains a magnified image of the sample, and which is located between the objective lens and the movable mirror used to direct the optical radiation transmitted through the sample either to the eyepiece or to the infrared detector.

In reflectance microscopy, the use of the approach outlined above introduces both an additional benefit and a problem. The benefit arises from the fact that the incident and reflected light paths are coincident in the plane of the adjustable field stop. The adjustable field stop thus acts to limit both the area illuminated by the incident radiation and the area viewed by the detector. This "double aperturing" serves to reduce the diffraction spread caused by the finite aperture stop (throughput-limiting aperture). In other words, the combination of an image-limiting field stop which is passed through by entering radiation (between the source and the sample) with an image-limiting field stop which is passed through by exiting radiation (between the sample and the detector) reduces the stray light due to the diffraction effect, and minimizes its negative effect on the image at the detector.

The problem associated with using an adjustable field stop common to both the incident and reflected beams results from the fact that radiation reflected from the "back" surface of the adjustable field stop will reach the IR detector, causing a significant "stray light" offset in the measured spectrum.

Light scattering from the rear of the adjustable field stop could be avoided by injecting the incident beam below the adjustable field stop. However, as discussed in the previous application, this may not be convenient in a particular microscope design. In addition, unless the field of view of the incident beam is limited by an adjustable field stop somewhere else in the optical train, an excess of IR radiation will be present in the region of the sample, and perhaps in the objective lens (depending on where the injection takes place). Some of this undesired radiation may be scattered into the system field-of-view, again leading to detected stray light.

A definition of terms relating to radiation "stops" may be useful at this point. As explained in the textbook "Fundamentals of Optics", by Jenkins and White, a stop (i.e., an element which limits the radiation passing through a given position) may be either an "aperture stop" or a "field stop". An aperture stop determines the amount of light reaching any given point in the image, and therefore controls the brightness of the image. A field stop determines the extent of the object, or the field, that will be represented in the image.

SUMMARY OF THE INVENTION

The present invention involves the combination of a plurality of innovations: (1) placing a variable field stop in a plane in which the incident beam is brought to a focus, and which is prior to the mirror used to superimpose the fields-of-view of the incident and detected beams; (2) selecting and positioning the various optical elements in such a way that such variable field stop is imaged in the plane which would normally contain the field-defining aperture in a transmission microscope; (3) illuminating by means of a visible light source, whose radiation can be switched onto the same path as the IR beam, so as to pass through the same variable field stop; and (4) providing means for viewing the visible light which is specularly reflected from the sample along a path which is coaxial with the path viewed by the IR detector.

As stated above, the present invention locates the effective adjustable field stop (hereinafter, the "first field stop") ahead of the injection mirror. This permits the adjustable field stop between the objective lens and the IR detector (hereinafter, the "second field stop") to remain open, at least initially. The size of the beam focused at the sample is thus controlled independently of the second field stop, which otherwise would cause back scatter, leading to stray light at the detector.

The optical elements of the microscope are so arranged that the first field stop is imaged in the plane which would provide the field defining stop in a transmission microscope.

In addition to avoiding the back scatter problem, the present invention permits a background-foreground visible lighting effect for the viewer when visible light is being used. Leaving the second field stop open allows a field-of-view larger than that provided by the first field stop. The effect is that the illumination defined by the first field stop provides a relatively bright, well-defined area on the sample, whereas the larger field permitted by the second field stop creates a larger, but less bright, viewing area (if additional light is introduced in the vicinity of the sample). In other words, the smaller, brighter area represents the spot which will be illuminated by the IR beam, whereas the larger, less bright area helps the viewer in adjusting the microscope.

DETAILED DESCRIPTION OF PREFERRED EMBODIMENT

Figure 1:
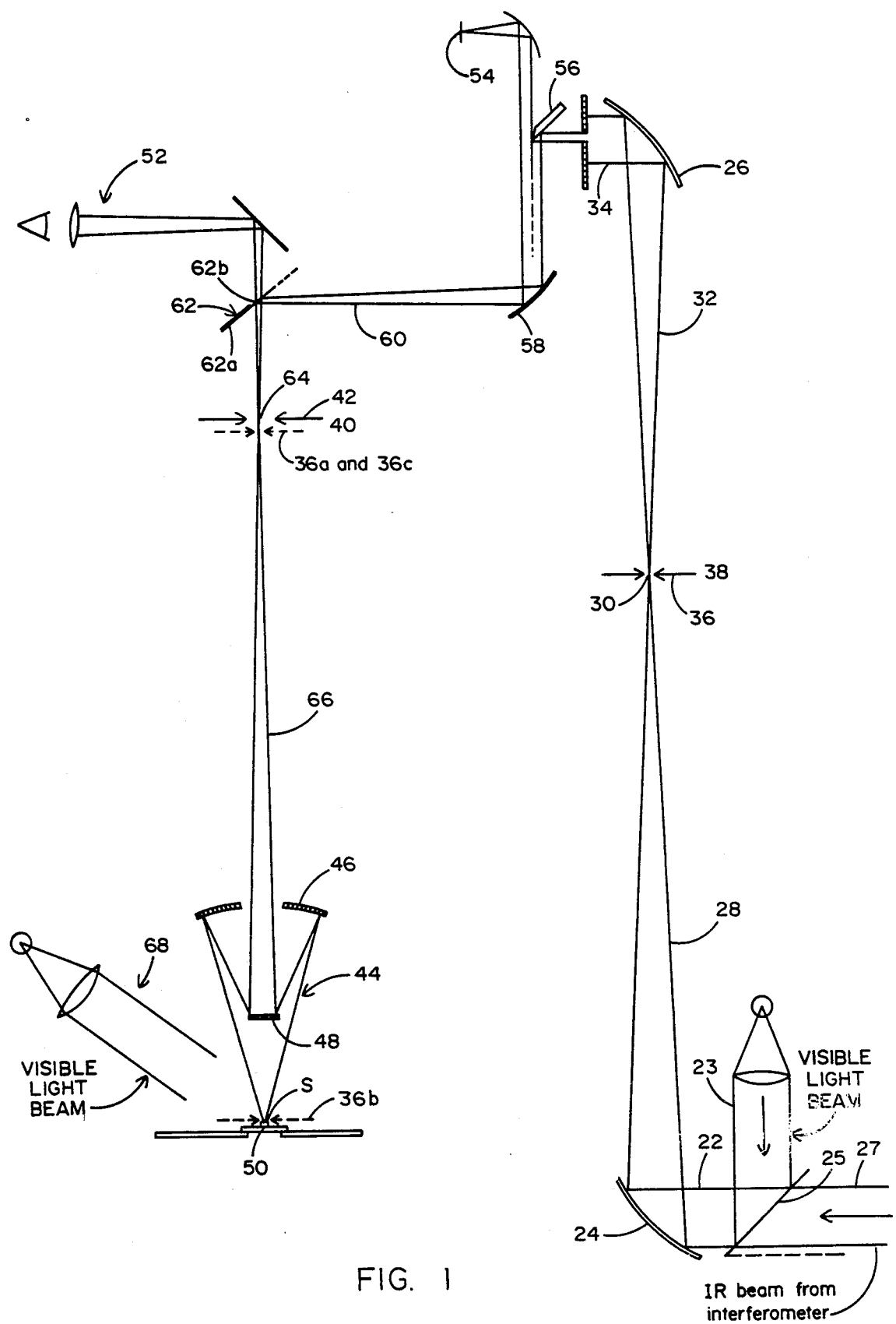
FIG. 1 is a schematic illustration of microscope radiation, incorporating the concepts of the present invention.

FIG. 1 shows schematically the radiation paths of the IR and visible light in a microscope unit incorporating the present invention. The general arrangement of the microscope structure corresponds to that shown in FIG. 2 of U.S. Ser. No. 907,993 and in FIG. 9 of U.S. Ser. No. 907,995 (The disclosures of those earlier filed applications are incorporated herein for clarification and additional detail).

A collimated beam 22 entering the microscope unit is reflected by a first parabolic mirror 24 toward a second, confocal parabolic mirror 26. Focusing beam 28, reflected from mirror 24, reaches a focus at 30, and thereafter, as diverging beam 32, reaches mirror 26, where it is reflected as a collimated beam 34. The entering collimated beam may be either a visible light beam 23, reflected by a flat mirror 25, or an IR beam 27 from an interferometer (with mirror 25 in its dashed line position).

An adjustable field stop 36 is located in the focal plane 38 of focal point 30. This is the adjustable field stop which was identified above as the first adjustable field stop. When the microscope is used in the reflectance mode, this adjustable field stop determines the effective field of view of the system. In other words, the adjusted size of this field stop determines the area of IR illumination at the sample.

An image of the first adjustable field stop 36 will be formed in the image plane 40 of a second adjustable field stop 42, which is located above an objective lens 44, preferably a Cassegrain objective having a larger mirror 46 and a smaller mirror 48.

A sample S is supported on a platform 50, the position of which may be adjusted in three axes by the operator. If the microscope is used in the transmission mode, the entering collimated beam is not reflected by mirror 24, but passes directly through the microscope structure to a short focal length reflector, which causes the radiation to focus at the sample on its way to the objective lens 44. If the beam is in the visible range it will be directed to an eyepiece 52; and if it is in the infrared range, it will be directed to a detector 54.

The adjusable field stop 42, referred to as the second adjustable field stop, is used to control the size of the area viewed at the sample when the microscope is operated in the transmission mode.

When the microscope is operated in the reflectance mode, the size of the illuminated area at the sample is controlled by the first adjustable field stop 36. In the reflectance mode, radiation at the sample comes from above, not below, the sample; and it passes downwardly through Cassegrain 44 before reflection, and upwardly through Cassegrain 44 after reflection. This radiation comes from beam 28-32-34, which is reflected into the microscope by an injection mirror 56. Mirror 56, as explained in application U.S. Ser. No 907,995 reflects half of the available collimated beam toward a parabolic mirror 58, from which it is reflected as a focusing beam 60. Beam 60 (after reflection by a flat mirror 62) focuses at 64, in the image plane 40, in which the second adjustable field stop 42 is located. Thereafter, a diverging beam 66 travels toward Cassegrain 44.

In the reflectance mode, the second adjustable field stop 42 is initially in open position. This avoids back scatter caused by reflection of incoming radiation by the upper surface of field stop 42. The first adjustable field stop 36 is used to control the size of the illuminated area at the sample. An image of field stop 36 will occur in the image plane 40 (the plane of field stop 42). This image of field stop 36 is identified as 36a, displaced slightly from field stop 42 for illustrative purposes. A second image of field stop 36, referred to as 36b, will be formed by objective lens 44 at the sample. This image will be reduced in diameter by an amount equal to the inverse of the magnification of the objective lens (typically 15x). After reflection from the sample, the radiation will again pass through the objective lens 44 and form a third image, identified as 36c, of adjustable field stop 36, in the same plane as 36a (assuming the microscope to be in proper focus).

In order to view the visible radiation transmitted by the first field stop 36, it is convenient to provide a semi-transparent beamsplitter at some point between the second field stop 42 and mirror 56. Alternatively, this could be accomplished by means of a movable, fully reflecting mirror between mirror 56 and the IR detector 54. In the present disclosure, a movable mirror 62 is shown, which has both a 100% reflecting region 62a, and a nominally 50% reflecting region 62b. For viewing the visible beam in reflectance, it is placed in the semi-transparent position, so as to direct part of the incident beam downward toward the sample, while allowing part of the reflected beam to pass through it and reach the eyepiece. This is an inefficient arrangement, but the losses are more than made up for by the fact that the sample will usually be on a specularly reflecting substrate, so that a large percentage of the incident radiation will be reflected in the appropriate direction to be collected by the objective lens and transmitted in the direction of the eyepiece.

When the microscope is being used to view a sample in transmission analysis, movable mirror 62 will be placed in the open position, so as to maximize the light reaching the eyepiece. During IR measurements (in either transmission or reflection), movable mirror 62 will be placed in the fully reflecting position. (Note that movable mirror 62 has three operative positions: fully-reflecting, partially-reflecting, and non-reflecting).

The projected field stop arrangement described above provides a somewhat different appearance to the viewer from that of conventional aperturing. This is due to two facts. First, the area of sample illumination is defined by highly directional light which is transmitted by field stop 36, is coaxial with the microscope optics, and is specularly reflected by the sample substrate. Second, the viewer's observed field-of-view is not closed down by field stop 42. Rather, he is able to view a relatively large area of the sample (given sufficient off-axis illumination as indicated by a visible light illuminator 68). The area to be illuminated by IR radiation is defined by the specularly projected image of te first adjustable field stop 36. The viewer sees this as a rather bright, well defined area on the sample. When the microscope is switched from its viewing mode to its IR measurement mode, the area illuminated by IR will be identical to this area, except for the diffraction spreading caused by the finite aperture of the objective lens.

Once the area to be illuminated for measurement has been properly defined by the use of the projected field stop, the second adjustable field stop 42 may be partially closed down, in order to eliminate the areas outside of the illuminated area from the measurement field-of-view. This serves to reduce measurement errors due to diffraction spread, by providing field stops for both the incident and emergent beams. As long as the surfaces of field stop 42 do not overlap the illuminated area as defined by 36a, the effects of spurious reflection from the rear surface of 42 should be insignificant.

As stated in the Background discussion, there is an inherent benefit due to the fact that radiation passes through a field stop both on its way to the sample and on its way to the detector after sample illumination. This is true whether it passes through the same field stop both as entering and as exiting radiation, or passes through one field stop as entering radiation and through a different field stop as exiting radiation. This benefit is the reduction of the diffraction effect, and is brought about by the "double aperturing" of the radiation.

The adjustable field stops 36 and 42 are sometimes referred to as apertures, although the term "field stop" is standard terminology in the optical design discipline. They function as field-defining stops, in that they control the size of the observed (illuminated) image. On the other hand, the term aperture, or aperture stop, is used in optical design terminology to identify the throughput-limiting aperture in the system, i.e., the most limiting "window" through which the available radiation must pass. In the present microscope, the throughput-limiting aperture is defined by the objective. Other optical elements in the system should be so designed as to ensure that the objective will receive the maximum number of optical paths which it can accept.

Figure 2:
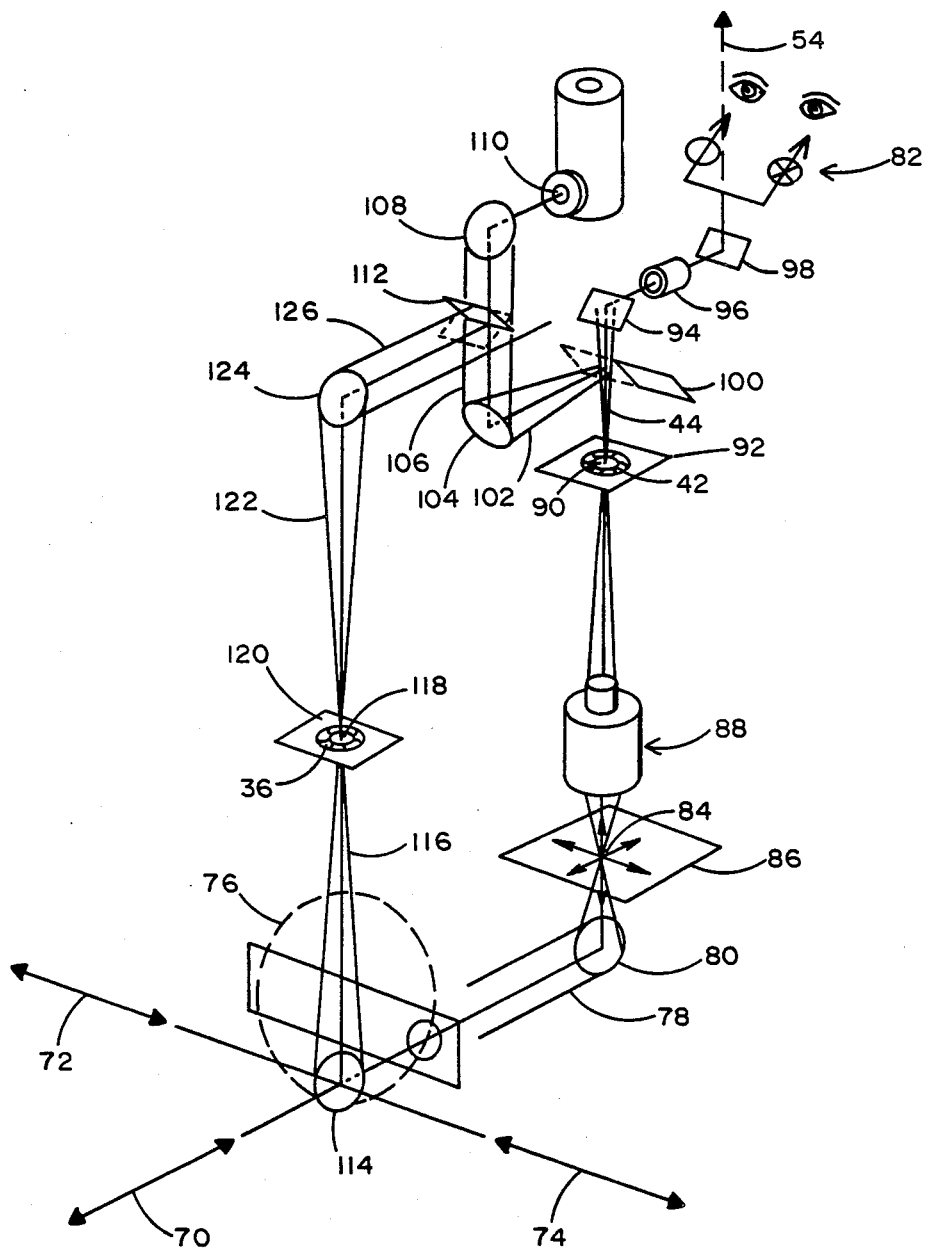
FIG. 2 is a diagrammatic showing of a microscope optical system adapted to use the present invention.

FIG. 2, which is almost identical with FIG. 1 of U.S. Ser. No. 907,993 provides a "summary" of a complete microscope unit. Three beam entry-exit directions are provided, symbolized by lines 70, 72 and 74, each of which has bi-directional arrows indicating that radiation may go into or out of the microscope in any of these three directions. The direction represented by line 70 is rearward from the microscope housing; the direction represented by line 72 is rightward from the microscope housing (as viewed from the front, or eyepiece, side); and the direction represented by line 74 is leftward from the microscope housing (as viewed from the front side). Generally, radiation entering along line 70 will be a collimated beam output by the interferometer (not shown).

After the entering beam, from any of the three directions, passes through its aperture into the microscope chamber, it will reach the position of a mirror-carrying wheel, or switch, indicated by dashed line 76. This wheel is an optical switching device which may be rotated to, and locked in position at, any one of six available positions. In at least one position, the wheel simply provides an aperture through which a collimated beam 78 entering on line 70 will pass directly to a parabolic mirror 80, which is used when the microscope is in the transmission mode. For viewing through an eyepiece 82 the incoming collimated radiation will be a collimated light, or visible, beam. For infrared analysis, the incoming radiation will be a collimated IR beam.

Parabolic mirror 80, which has a short focal length, causes the reflected beam 78 to focus at point 84, which is the sample location. The sample is supported in its image plane on a platform 86, which is position-adjustable under operator control in X, Y and Z axes, in order to bring the sample into the focal point After passing through the focal point, the diverging rays of the radiation beam enter a Cassegrain objective 88, which contains reflective surfaces for microscopic viewing of the sample. The focusing beam leaving objective 88 reaches its focal point at 90, which is in an image plane 92 containing the second adjustable stop (or iris) 42 (see FIG. 1), the size of which is adjustable under operator control.

After focusing in image plane 92, the diverging beam is reflected by a flat mirror 94 into an image transfer lens 96, from which the exiting beam is directed by another flat mirror 98 to eyepiece 82 for binocular viewing, and also for position adjustment by the operator.

Note that a flat, movable view/test mirror 100 ( which corresponds to mirror 62 in FIG. 1) is in its solid line position during visual inspection, and position-location, of the sample. Mirror 100 is moved to its dashed line position when infrared radiation is being transmitted through the microscope. In the infrared transmission mode, IR radiation from the interferometer, entering along path 70, follows the same path as that described for the visible radiation, until it is reflected by mirror 100 to provide diverging beam 102.

Beam 102 is recollimated by a parabolic mirror 104, and directed as beam 106 toward another parabolic mirror 108, which causes the radiation to focus at a detector 110. Note that a movable mirror 112, in this mode, must be in a position in which it does not block the collimated beam 106. Mirror 112 has a total of three available positions, two of which are reflecting positions, as will be explained below.

In one or more positions of mirror-carrying wheel 76, the entering collimated radiation will be reflected by a parabolic mirror 114 on the wheel to provide focusing radiation 116 directed toward focal point 118. Focal point 118 is in an image plane 120 containing the first adjustable field stop (or iris) 36 (see FIG. 1), the size of which is adjustable under operator control. After focusing at 118, a diverging radiation beam 122 will be reflected and recollimated by a parabolic mirror 124.

The radiation path between confocal paraboloids 114 and 124 is a radiation path separate from that of the radiation passing through objective 88. This separate path provides a plurality of advantages for the microscope accessory unit, as discussed in U.S. Ser. No. 907,993 and U.S. Ser. No. 907,995. In the present application it provides another benefit, which is of vital importance. It permits the first adjustable feld stop to control the field of view at the sample-located reflecting focal plane, with the advantages discussed above in the explanation of FIG. 1.

In the reflectance mode, collimated beam 126, reflected by mirror 124, will be partially reflected by movable mirror 112. This is a 100% reflective mirror, which has been moved to a position in which it reflects half of beam 126 toward the Cassegrain lens 88 and the sample at 84. This 50% beam is caused by parabolic mirror 104 to focus at point 90 in focal plane 92, having been reflected toward that point by flat mirror 100, which has been moved into its dashed line position. This radiation will, as explained in detail in U.S. Ser. No. 907,995 pass downwardly through Cassegrain 88, be reflected by the sample at 84, pass upwardly through Cassegrain 88, and pass through focal point 90. It will then be reflected by flat mirror 100, and be recollimated by parabolic mirror 104 in the form of a 50% beam which bypasses mirror 112, and reaches detector 110.

Figure 3:
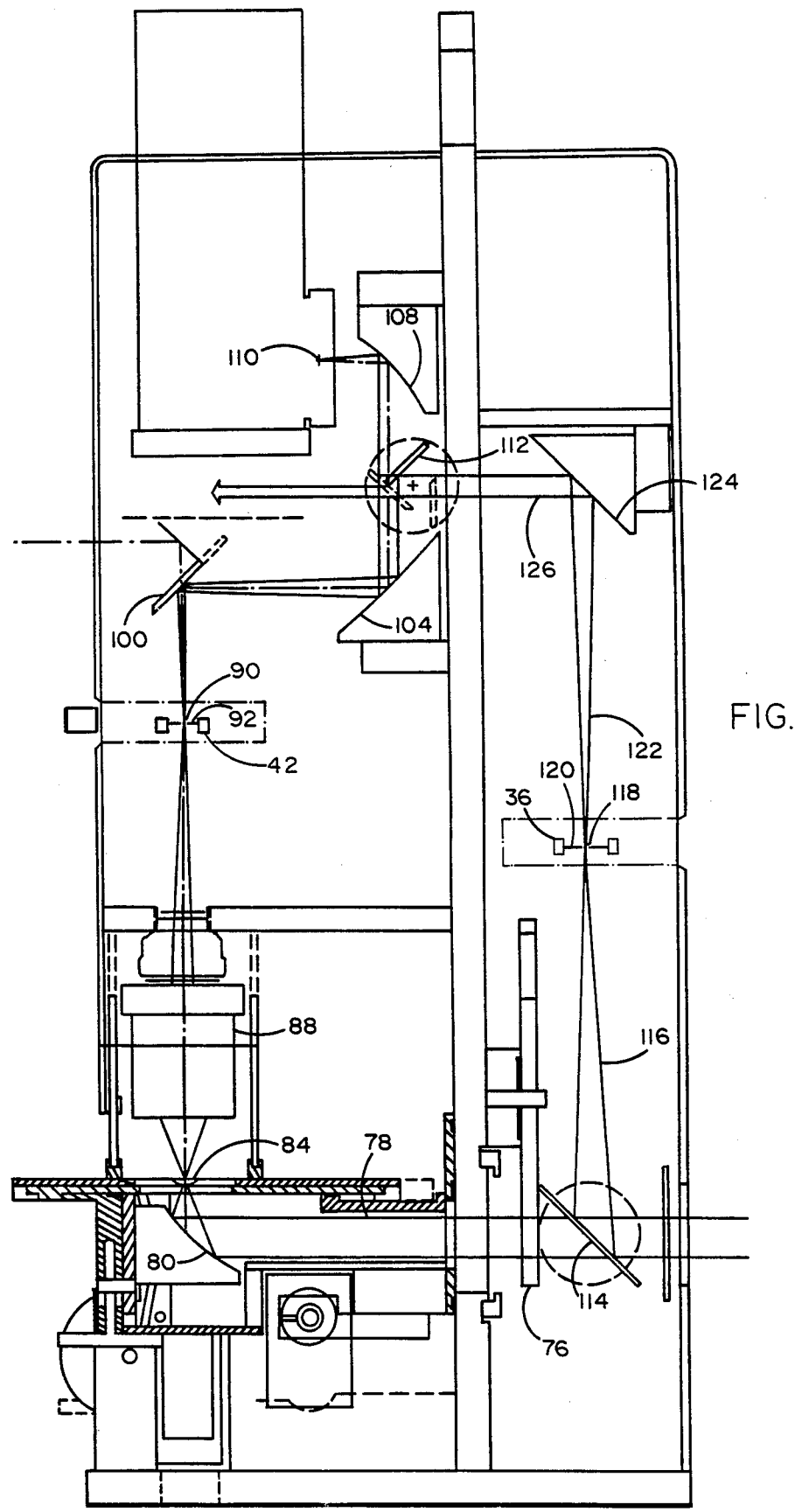
FIG. 3 is a side view of a microscope unit incorporating the primary components capable of providing the benefits of the present invention.

FIG. 3 is a side elevation view showing the internal elements of an actual microscope accessory unit, which provides the projected field stop function of the present invention. The same numerals are used in FIG. 3 as in FIG. 2. Note that the first adjustable field stop 36 may be used to determine the size of the beam focused at the sample in the reflectance mode. Since the second adjustable field stop 42 is not used for this purpose, radiation back scatter resulting from reflection by the upper side of field stop 42 is substantially avoided. This also permits the focused center point to be viewed by the operator against a background of larger area, but less brightness (assuming visible background light is made available, as shown at 68 in FIG. 1).

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In a microscope having a sample supporting member which retains a sample in a sample image plane, an objective, a detector of infrared radiation, and means for causing an infrared radiation beam to enter the microscope, an optical system having a reflectance mode for sample viewing, comprising:
    means for reflecting the entering radiation beam into the objective in such a way that it passes through the objective on its way to the sample, is reflected at the sample, and travels back through the objective on its way to the detector;
    means through which image plane the radiation passes as it moves toward the sample, but not as it moves from the sample toward the detector for providing a first image plane between the entering radiation and the reflecting means;
    means for providing a second image plane between the objective and the detector; and
    an adjustable field stop which is located at the first image plane, and which is adjustable so as to determine the size of the illuminated area at the sample when the sample is viewed in the reflectance mode;
    the image at the adjustable field stop being reimaged at the second image plane and at the sample when the sample is viewed in the reflectance mode.

2. The microscope of claim 1 which also comprises:
    another adjustable field stop which is located at the second image plane.

3. The microscope of claim 2 which also comprises:
    means for supplying visible light through the adjustable field stop located at the first image plane, in order to permit observation of the illuminated area of the sample; and
    separate means for supplying visible light to permit simultaneous observation of the area surrounding the illuminated area of the sample.

4. In a microscope having a sample supporting means, means for directing an entering radiation beam into the microscope, and a detector for receiving the beam after it has illuminated the sample:
    means for providing a first image plane at the sample location;
    means for providing a second image plane at the detector location;
    an objective between the first image plane and the second image plane;
    means for illuminating the sample by causing the entering radiation to be transmitted through the sample and thence through the objective;
    means for providing a third image plane between the objective and the detector;
    an adjustable field stop located at the third image plane, which stop is adjustable so as to determine the size of the area at the sample illuminated by the radiation which is transmitted through the sample;
    a mirror positioned to reflect entering radiation toward the sample, so that such radiation is reflected at the sample, such radiation being focused in the third image plane on its way to the sample;
    means for providing a fourth image plane between the entering radiation and the mirror; and
    another adjustable field stop located in the fourth image plane, which stop is adjustable so as to determine the size of the area at the sample illuminated by the radiation which is reflected at the sample.

5. The microscope of claim 4 in which the adjustable field stop in the third image plane is adjustable to block stray light from the detector when the radiation is reflected at the sample.

6. The microscope of claim 4 in which the radiation reflected by the mirror toward the sample passes through the third image plane in one direction moving toward the sample, and in the opposite direction moving away from the sample.

7. A method of microscopically viewing a sample both in the visible and in the infrared radiation wavelengths, comprising:
    directing a first visible beam through a first field stop to illuminate the sample;
    adjusting the first field stop to control the area of illumination at the sample;
    directing a second visible beam to illuminate the sample;
    viewing the sample through a second field stop with the second field stop in a relatively open position, in order to illuminate an area surrounding the area of illumination permitted by the first field stop;
    adjusting the sample position to provide the desired location of sample illumination by radiation passing through the first field stop;
    adjusting the second field stop to reduce the diffraction effect of the infrared radiation; and
    illuminating the sample by an infrared beam which is thereafter directed to a detector.

8. The method of claim 7 in which the infrared beam diffraction effect is reduced by a field stop both as the beam travels toward the sample and as the beam travels from the sample toward the detector.

* * * * *

UNITED STATES PATENT AND TRADEMARK OFFICE
CERTIFICATE OF CORRECTION

PATENT NO. : 4,843,242
DATED : June 27, 1989
INVENTOR(S) : Walter M. Doyle

It is certified that error appears in the above-identified patent and that said Letters Patent is hereby corrected as shown below:

Column 1, line 26: After "injection" insert -- mirror. --

Column 5, line 63: After "collimated" insert -- white --

Column 7, line 39: After "means" insert -- for providing a first image plane between the entering radiation and the reflecting means, --

Column 7, lines 41-43: Delete "for providing a first image plane between the entering radiation and the reflecting means --

Signed and Sealed this

Twentieth Day of March, 1990

Attest:

JEFFREY M. SAMUELS

Attesting Officer

Acting Commissioner of Patents and Trademarks